United States Patent [19]

Flemer, III

[11] Patent Number: Plant 7,072

[45] Date of Patent: Dec. 12, 1989

[54] AMELANCHIER CANADENSIS "WHITE PILLAR"

[75] Inventor: William Flemer, III, Princeton, N.J.

[73] Assignee: Newplant Associates, Princeton, N.J.

[21] Appl. No.: 206,412

[22] Filed: Jun. 13, 1988

[51] Int. Cl.[4] ..... A01H 5/00

[52] U.S. Cl. ..... Plt./51

[58] Field of Search ..... Plt./51

*Primary Examiner*—James R. Feyrer

*Attorney, Agent, or Firm*—Frank B. Robb

[57] ABSTRACT

An *Amelanchier canadensis* tree grown in a cultivated area of a nursery near Princeton, N.J., which tree is distinctly columnar in overall appearance in contrast to other *Amelanchier canadensis* trees which are much more spreading, the instant variety being resistant to leaf spot fungi which causes defoliation of the usual Amelanchier trees in warm, humid weather, and the very abundant blooms of the tree which substantially hide the branches, the fall colors of its leaves providing a mixture of reds and purples.

2 Drawing Sheets

In the course of breeding and growing various ornamental trees, a program which is long continuing and comprises a wide variety of such ornamental varieties, particularly trees, I have had occasion to grow the usual *Amelanchier canadensis* trees in substantial numbers and am familiar therefore with the common characteristics of such trees.

As will be recognized, the *Amelanchier canadensis* tree is usually and commonly called the Shadblow tree, and this particular variety is most outstanding from several aspects because as it was growing as a seeding, it was noticeable in a group of other *Amelanchier canadensis* trees growing in a cultivated area because the instant variety is of a substantially more upright columnar configuration than the usual trees of this variety, which are spreading and of much wider aspect.

The columnar arrangement is desirable under many conditions and makes the tree an outstanding variety for decorative uses. Thus the commercial designation I have chosen, "White Pillar" is particularly appropriate.

The tree was first noticed as before stated, in a very large block of Amelanchier seedlings which themselves had been grown from seed collected on the grounds of the nursery with which I am connected.

The usual spreading clumps of sister seedlings, made the instant variety outstanding because of its narrow upright growth and dark green foliage.

It is further characterized by the fact that it is not defoliated by leaf spot funi which is the case in the usual Amelanchier seedlings, in warm humid summers.

The instant variety retained all its leaves in those circumstances when the other trees of the Amelanchier variety lost theirs.

The instant variety has established itself as a very abundant bloomer, and the flowers even though small are so densely borne as to hide the branches of the tree.

In the fall the colors presented by the overall appearance of the tree are a glowing mixture of red and purple shades.

Other than the foregoing differences established, it has the usual characteristic colors of the *Amelanchier canadensis* and otherwise is quite similar as to the shapes of its leaves and other aspects.

There is supplied and attached hereto an illustration of a block of the specimens of the variety which have been reproduced asexually by grafting on potted seedlings in the greenhouse.

Figure 1:
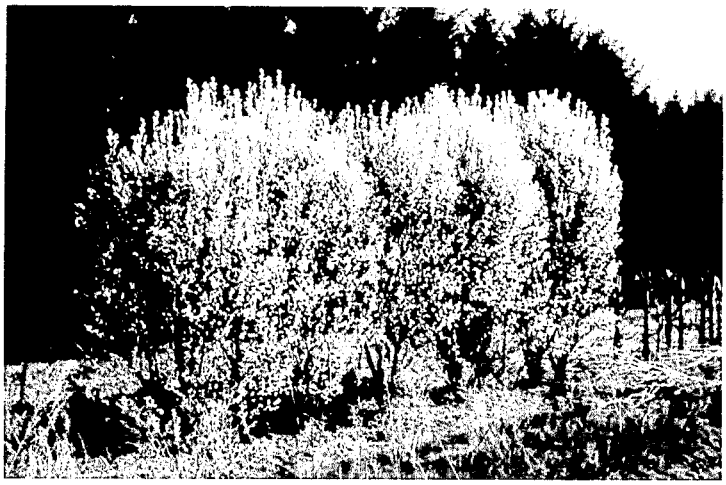
FIG. 1 of the drawing is a color photograph of a row of specimens of 'White Pillar' at a stage approaching full bloom.
Figure 2:
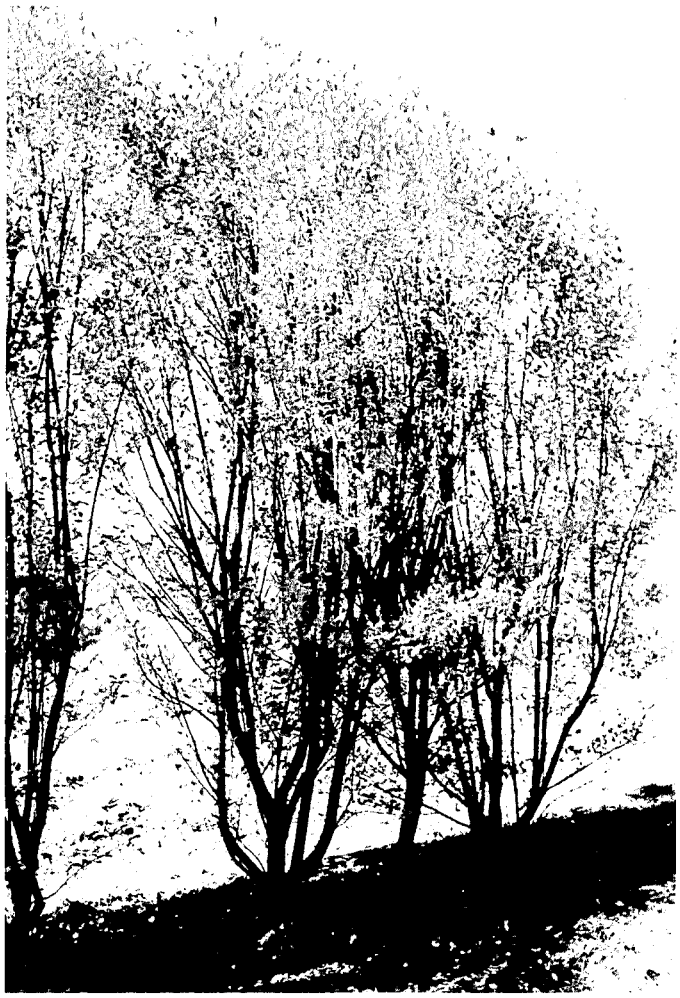
FIG. 2 is a closer color photograph showing fall coloration, excellent fall leaf retention and the unique branching habit of 'White Pillar'.

The illustration in the drawing shows several trees in a row, and discloses the upright nature thereof along with the white coloring which is so characteristic, the colors of the leaves obviously not being clearly disclosed but being noticeably moderate olive green, as compared with the Munsell Color Chart produced by the Munsell Color Company of Baltimore, Md.

In all cases where color is other than common by way of description, and is related to a chart for differences, the Munsell Color Chart is used in that connection. There follows a detailed description of the variety, it being noted that the trees disclosed were grown in Plainsboro Township, N.J.

DETAILED BOTANICAL DESCRIPTION

Parentage:

*Seed parent.*—Unknown.

*Pollen parent.*—Unknown.

*Newly found seedling of.*—*Amelanchier canadensis.*

Tree: Small; very upright and narrow (2.5 meters wide); medium tall (6 meters) and dense; and hardy.

*Trunk or mature stems.*—Slender and smooth.

*Color.*—Pale grey.

*Branches.*—Slender and smooth abundant; dense. Color — Moderate reddish brown, 2.5 YR 3/3. Lenticels — Sparse. Habit — Side branches erect; closely appressed to trunk or stems. Crotch angle — 10 to 14 degrees from trunk or stems.

*Leaves.*—Quantity abundant, leathery, and thick. Length — 5 to 6 cm. Width — 3 cm. Shape arrangement — Alternately around stems. Glabrous shape—Ovate. Color — Summer, moderate olive green 5 GY 4/3. Upper and lower surfaces essentially the same. Fall, moderate red 2.5R 4/10. Margin — Minutely serrate. Petiole — Short, 2 cm long. Glands — None.

*Flower buds.*—Very hardy, pointed. Size — 1 cm long. Shape — Slender, ovate. Color — Dark greenish yellow, 10Y 6/7.

*Flowers.*—Dates first bloom, April 10th in Central New Jersey. Dates full floom, April 15th in Central New Jersey. Quantity — Very abundant so densely borne as to hide stems. Fragrance — None. Size — Small in 8 flowered to 10 flowered racemes.

*Petalage.*—Number of petals, 5. Shape of petals, ovate. Length — 1 cm; width 0.4 cm. Color — White.

*Fruits.*—When borne, June. Abundance — Sparse. Size — 1 cm across. Color — Purple.

I claim:

1. A new and distinct variety of *Amelanchier canadensis* tree substantially as herein shown and described, characterized particularly as to novelty by its very narrow, upright growth, dark green foliage which is much more resistant to defoliation by leaf spot fungi, in warm, humid weather than other seedlings of the variety, its blooms, which though small are so densely borne as to hide the branches, and glowing mixture of red and purple shades of leaves in the fall.

* * * * *